United States Patent
Mason et al.

[11] Patent Number: 5,879,379
[45] Date of Patent: Mar. 9, 1999

[54] FACIAL HEAT TRANSFER DEVICE WITH PLURAL CONTAINERS

[76] Inventors: Patricia T. Mason, 141 Brinkwood Rd., Brookeville, Md. 20833; Sarah Beta Schroder, 3435 R St. NW, #24, Washington, D.C. 20007

[21] Appl. No.: 882,117

[22] Filed: Jun. 25, 1997

[51] Int. Cl.[6] .................................. A61F 7/00; A61F 7/10
[52] U.S. Cl. ............................................ 607/109; 607/108
[58] Field of Search ...................................... 607/108, 109

[56] References Cited

U.S. PATENT DOCUMENTS

| | | |
|---|---|---|
| 702,759 | 6/1902 | Allegretti . |
| 1,860,847 | 5/1932 | Armstrong . |
| 2,038,275 | 4/1936 | Fogg . |
| 2,101,628 | 12/1937 | Padelford . |
| 2,237,971 | 4/1941 | Padelford . |
| 2,477,883 | 8/1949 | Lefohn . |
| 2,626,343 | 1/1953 | Fogel et al. . |
| 2,796,903 | 6/1957 | Gazelle . |
| 3,195,539 | 7/1965 | Hyman . |
| 3,491,761 | 1/1970 | Baker . |
| 3,606,890 | 9/1971 | Gilbert . |
| 4,190,054 | 2/1980 | Brennan . |
| 4,243,041 | 1/1981 | Paul . |
| 4,559,047 | 12/1985 | Kapralis et al. . |
| 4,614,189 | 9/1986 | MacKenzie . |
| 5,020,536 | 6/1991 | Keen . |
| 5,119,812 | 6/1992 | Angelo . |
| 5,314,456 | 5/1994 | Cohen . |
| 5,395,400 | 3/1995 | Stafford et al. . |
| 5,409,500 | 4/1995 | Dyrek . |
| 5,628,772 | 5/1997 | Russell .................................... 607/109 |
| 5,728,146 | 3/1998 | Burkett et al. ........................... 607/109 |

*Primary Examiner*—William E. Kamm
*Assistant Examiner*—Carl H. Layno
*Attorney, Agent, or Firm*—Birch, Stewart, Kolasch & Birch, LLP

[57] ABSTRACT

An inexpensive heat transfer device which is readily pliable at freezing temperatures conforms to living tissue regions. The heat transfer device conforms to the contours of the living tissue to facilitate heat transfer between the device and the tissue regions which in turn reduces pain or swelling in the tissue regions from surgical procedures. The heat transfer device includes a first container and several second smaller containers disposed and freely flowable in the first container.

23 Claims, 2 Drawing Sheets

FACIAL HEAT TRANSFER DEVICE WITH PLURAL CONTAINERS

1. Field of the Invention

The present invention generally relates to a heat transfer device for reducing swelling in human tissue after surgical face and neck procedures. The heat transfer device may be utilized to apply heat or cold to the human tissue areas.

2. Description of the Background Art

Various therapeutic cold packs and facial treatment masks are known in the art. These treatment masks and cold packs employ many different types of heat transfer materials. Some of these heat transfer materials include gelatinous substances such as COLD ICE™, water, water-based gels and hydrophilic gels such as CRYOGEL™. When water alone is used as the heat transfer material for applying cold. At freezing temperatures, the water becomes very rigid in the form of ice and is not pliable to conform to the tissue region. Furthermore, if gelatinous substances are used, they significantly add to the cost of manufacturing the treatment masks or cold packs.

Accordingly, a need in the art exists for a heat transfer device which is readily pliable at freezing temperatures and which is relatively inexpensive to make.

SUMMARY OF THE INVENTION

It is the primary object of the present invention to provide a heat transfer device which is readily pliable at freezing temperatures to conform to the intended covered tissue region while the manufacturing costs of the heat transfer device are relatively low.

It is additionally a further object of the present invention to provide a heat transfer device which is readily pliable to conform to the contours of the human face to reduce pain or swelling.

Another object of the present invention is to provide a heat transfer device which conforms to the contours of a neck region of the human body to reduce pain or swelling.

These and other objects of the present invention are fulfilled by providing a heat transfer device comprising a first container having an open interior, the first container being flexible; means for transferring heat including a plurality of second containers, the second containers being freely flowable within the interior of the first container such that the second containers are readily movable relative to one another, the means for transferring heat further including a material conducive for heat transfer, at least some of the second containers being filled with the material, the first container being placeable on a living tissue region whereafter first and second containers conform to the tissue region, the means for transferring heat providing heat transfer between the first container and the tissue region to reduce at least one of pain and swelling in the tissue region.

In addition, these and other objects of the present invention are also accomplished by a method of reducing swelling in living tissue with a heat transfer device, comprising the steps of: placing a first container having a plurality of second spherical shaped containers disposed therein into at least one of a heating device and a refrigerating device; placing the first container over a tissue region; conforming a shape of the first container and second containers to the tissue region; and fastening the first container to the tissue region with a tie device, whereby the heat transfer device provides heat transfer between the first container and the tissue region to reduce at least one of pain and swelling in the tissue region.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
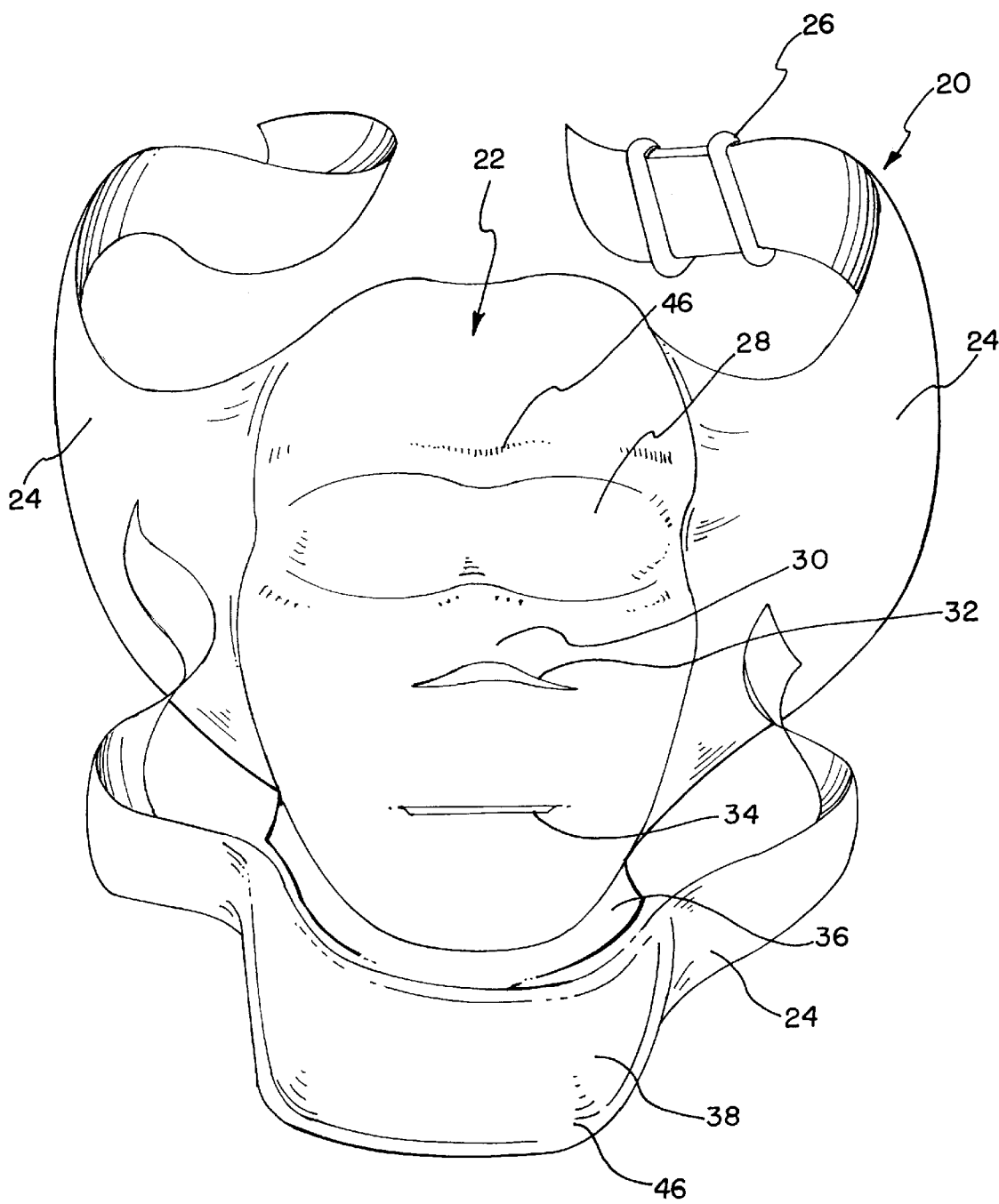
FIG. 1 shows a front view of a first embodiment of the heat transfer device.

Referring in detail to the drawings and with particular reference to FIG. 1, a heat transfer device 20 is shown in the form of a facial mask and neck bandage. The heat transfer device is not limited to these shapes and can be formed into any number of shapes and sizes that conform to a specific region of living tissue. The embodiment shown in FIG. 1 is designed for the human anatomy, however, the heat transfer device may be designed for other living tissues such as plants or animals, and therefore the heat transfer device will be shaped accordingly.

The heat transfer device can be either heated or cooled depending on the medical condition of the living tissue. For example, to reduce swelling after surgical face and neck procedures, the heat transfer device is preferably cooled by a refrigeration unit and then placed on the living tissue to reduce swelling and/or pain. If the medical condition involves head aches or sinus tension due to head colds, the heat transfer device is preferably heated by some heating unit, such as a microwave oven, so that the heat transfer device alleviates sinus congestion or pain from the head aches. In the situation where the user desires relaxation therapy, the heat transfer device is preferably heated where the heat transferred from the heat transfer device soothes and relaxes the user.

As shown in FIG. 1, the heat transfer device includes a first container 22 which is shaped in the form of a human facial region. A first container 22 includes a tie device 24 which is made from material extending from the first container 22. While the tie device is preferably made from extension of the material of the first container 22, other tie devices such as cloth straps, leather straps, cloth straps with VELCRO™ (hook and loop type fasteners) or the like may be employed. The tie device 24 further includes a fastening mechanism in the form a clip 26 which permits the end of each tie device 24 to be connected to each other. The fastening mechanism is preferably a clip but other fastening mechanisms such as snaps, buttons, or hook and loop type fasteners may be employed. It is noted that the tie device 24 permits the user to have increased mobility where the user can move his head or neck freely without the need to provide manual support to the first container 22.

The first container 22 further includes concave eye-shaped surface regions 28 which conform to the surface area of eyes of a human body. It is noted that instead of concave eye-shaped surface regions 28 the first container may employ openings therethrough to permit the user to see through the first container 22. Alternatively, transparent material could be provided in regions 28. The first container 22 further includes an elevated nose-shaped surface region 30 which conforms to the shape of a human nose. Beneath the elevated nose-shaped surface region 30, the first container 22 further includes a nostril-shaped orifice 32. This nostril-shaped orifice may include any number of shapes such as two holes, a slit, or the like.

The first container 22 further includes a second mouth-shaped orifice 34 which conforms to the mouth of a user to permit breathing therethrough. It is noted that the mouth-shaped orifice can take on any number of shapes such as a series of circular holes, a slit, or a mesh material, or the like. The first container further includes a fastening device 36 which permits the attachment of a supplemental container 38. The fastening device 36 is preferably VELCRO™ (hook and loop type fasteners) which permits rapid and easy attachment and the detachment of the supplemental container 38. The fastening device 36 is not limited to VELCRO™ and can include other fastening devices such as zippers, buttons, or other like structures.

The supplemental container 38 is made similar to the first container 22 but is shaped in the form of a neck region of the human body. However, as noted above, the shapes of the first container 22 and the supplemental container 38 are not limited to the facial regions and neck regions of the human body. Other shapes of the containers include rectangular (for use in knee or elbow applications), or polygonal shapes (for applications such as the shoulders and back of the human body), or the like.

The first and supplemental containers, 22 and 38, respectively, further include a fabric material 46 on their respective outer surfaces. This outer fabric material 46 is designed to come in contact with any post-operative drainage or secretions of wounds secreting from the living tissue which is covered by the containers. The outer fabric material 46 is preferably mole skin or water proof soft paper. However, other materials such as gauze, gauze and mesh material combined, or other like structures may be employed. The first container 22 may also be provided with disposal pads made from the outer fabric material 46 to recover the first container 22 as necessary.

Figure 2:
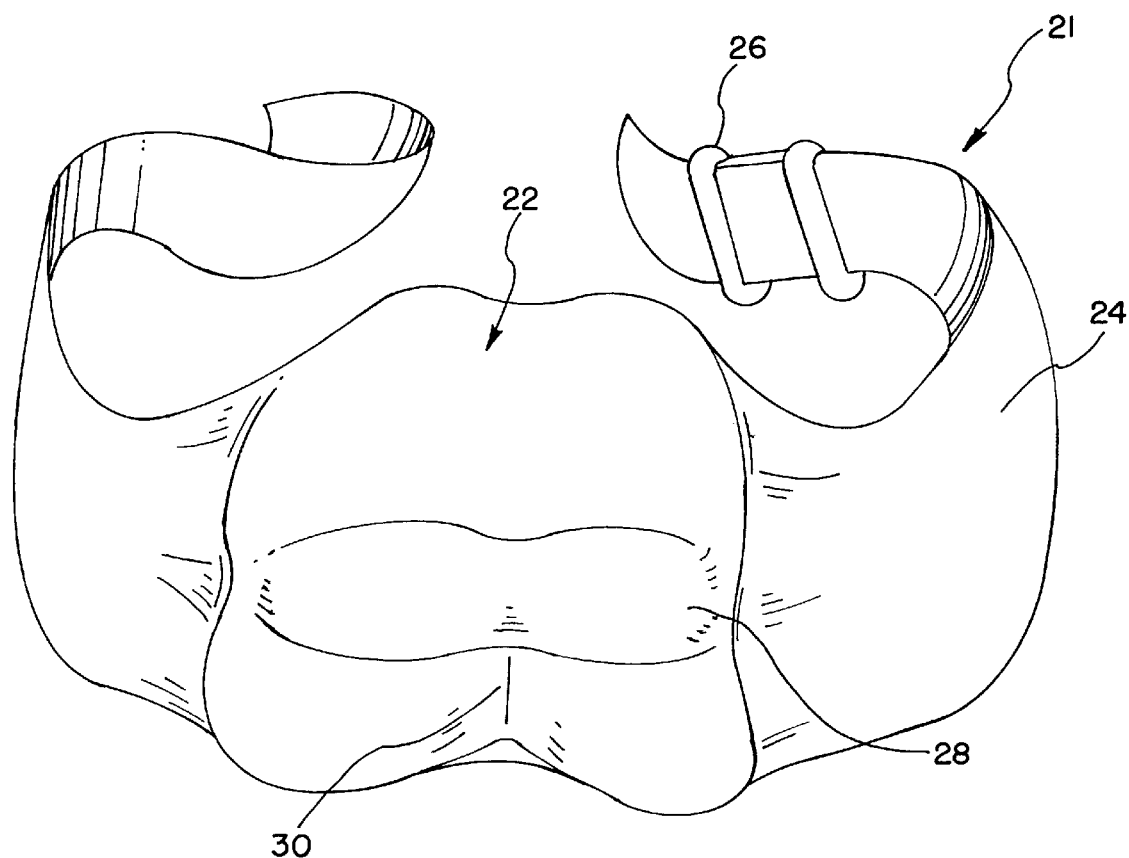
FIG. 2 shows a front view of a second embodiment of the present invention.

In FIG. 2, a second embodiment of the present invention is shown. In this embodiment, the first container 22 is in the shape of the upper portion of a human face. The container 22 in this embodiment is designed to facilitate heat transfer between the heat transfer device and specific regions of the user's face.

Figure 3:
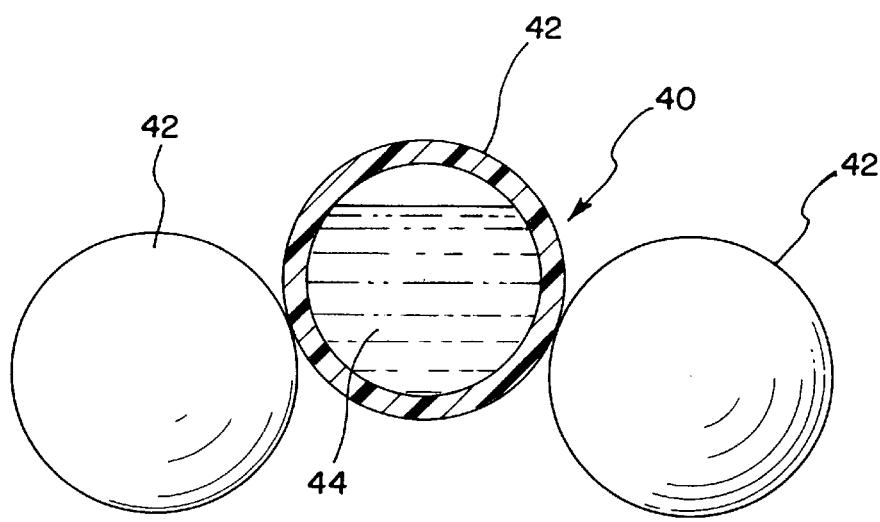
FIG. 3 shows a cross section of the means for heat transfer of the present invention.

In FIG. 3, the means for transferring heat 40 is shown. The means for transferring heat 40 includes a plurality of second containers 42 which are spherically shaped. The shape of these containers is not limited to spheres, and can include other shapes such as cuboids, prisms, polyhedrons, and the like. Each second container 42 is preferably filled with a material 44 conducive for heat transfer. Preferably, this material 44 includes water. However, other materials such as water-based gels or other gelatinous substances or mixtures thereof or the like may be employed. The second containers 42 are preferably completely filled with the material 44, however, it is possible to partially fill the second containers 42 with the material 44 and obtain successful heat transfer. It is noted that a mixture of empty second containers 42 and filled second containers 42 may be employed to also obtain successful heat transfer results.

The second containers 42 are preferably made from a plastic composition. However, the second containers 42 are not limited to the plastic composition and may include other compositions such as rubber, rubber-plastic mixtures, or the like where the chemical composition of the second containers prevent the material 44 from permeating through the walls of the second containers 42. The means for transferring heat 40 is not limited to the second containers 42 and can include a mixture of the second containers and other substances such as water-based gels, gelatinous substances, or ammonium nitrate granules and water. The second containers 42 preferably have a diameter of 0.5 centimeter but other sizes may be employed depending upon the amount of heat transfer and flexibility required by the intended covered tissue region. The second containers 42 provide a reusable material which can be refrozen or reheated while still maintaining its pliability to permit the first container 22 and second containers 42 to conform to living tissue regions.

Apart from the heat transfer device, a method for reducing at least one of pain and swelling in living tissue is disclosed by the present invention. In this method, the step of placing a first container having a plurality of second spherically shaped containers disposed therein into at least one of a heating unit and a refrigerating unit is provided. Next, the first container 22 is placed over a tissue region. The first container 22 and second containers 42 are then conformed to the shape of the tissue region. The first container 22 is then fastened to the tissue region with a tie device 24 whereby the heat transfer device 20 provides heat transfer between the first container 22 and the tissue region to reduce at least one of pain and swelling in the tissue region. The invention provides for a method where the fastening step further includes the step of attaching two ends of a tie device with a clip 26. The method further includes the step of placing a third container 38 having a plurality of second spherically shaped containers 42 disposed therein into at least one of a heating device and a refrigerating device. The method further includes a step of placing the third container 38 over a tissue region while attaching the third container to the first container 22 by a hook and loop type fastener 36.

The first container 22 and supplemental container 38 provide an inexpensive heat transfer device which is readily pliable at freezing temperatures to conform to intended covered tissue regions. The first and supplemental containers provide a heat transfer devices which are readily pliable to conform to the contours of a face and contours of a neck region of the human body.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A heat transfer device comprising:

a first container having an open interior, the first container being flexible;

means for transferring heat including a plurality of second containers, the second containers being freely flowable within the interior of the first container such that the second containers are readily movable relative to one another, said means for transferring heat further including a material conducive for heat transfer, at least some of the second containers being filled with said material, the first container being placeable on a living tissue region whereafter first and second containers conform to the tissue region, said means for transferring heat providing heat transfer between the first container and the tissue region to reduce at least one of pain and swelling in the tissue region, said first container has a shape in the form of said tissue region wherein said first container has a human-face shape with concave eye-shaped surface regions, said first container further includes an elevated nose-shaped surface region.

2. The heat transfer device of claim 1, wherein a majority of the second containers has a substantially spherical shape.

3. The heat transfer device of claim 2, wherein a majority of the second containers comprises a plastic material.

4. The heat transfer device of claim 1, wherein said material is water whereby said heat transfer device comprises at least one of being frozen and heated to initiate heat transfer between said first container and the tissue region.

5. The heat transfer device of claim 1, wherein said first container further includes a nostril-shaped orifice.

6. The heat transfer device of claim 5, wherein said nostril-shaped orifice is a first orifice, and said container device further includes a second mouth-shaped orifice.

7. The heat transfer device of claim 1, wherein said first container and second containers comprise a plastic material.

8. A heat transfer device comprising:
a first container having an open interior, the first container being flexible;
means for transferring heat including a plurality of second containers, the second containers being freely flowable within the interior of the first container such that the second containers are readily movable relative to one another, said means for transferring heat further including a material conducive for heat transfer, at least some of the second containers being filled with said material, the first container being placeable on a living tissue region whereafter first and second containers conform to the tissue region, said means for transferring heat providing heat transfer between the first container and the tissue region to reduce at least one of pain and swelling in the tissue region, said first container further includes a first fastening device attached to edges of said container device; and
a third container having a plurality of said second containers, said third container includes a second fastening device mating with said first fastening device, said second fastening device is connected to an edge of a second container device.

9. The heat transfer device of claim 8, wherein each fastening device includes a hook and loop type fastener.

10. The heat transfer device of claim 8, wherein said first container device has a human face shape and said third container device has a neck shape.

11. The heat transfer device of claim 8, wherein a majority of the second containers has a substantially spherical shape.

12. The heat transfer device of claim 8, wherein said material is water whereby said heat transfer device comprises at least one of being frozen and heated to initiate heat transfer between said first container and the tissue region.

13. A heat transfer device comprising:
a first container having an open interior, the first container being flexible;
means for transferring heat including a plurality of second containers, the second containers being freely flowable within the interior of the first container such that the second containers are readily movable relative to one another, said means for transferring heat further including a material conducive for heat transfer, at least some of the second containers being filled with said material, the first container being placeable on a living tissue region whereafter first and second containers conform to the tissue region, said means for transferring heat providing heat transfer between the first container and the tissue region to reduce at least one of pain and swelling in the tissue region, said first container has a rectangular shape.

14. The heat transfer device of claim 13, wherein a majority of the second containers has a substantially spherical shape.

15. The heat transfer device of claim 13, wherein said material is water whereby said heat transfer device comprises at least one of being frozen and heated to initiate heat transfer between said first container and the tissue region.

16. A heat transfer device comprising:
a first container having an open interior, the first container being flexible;
means for transferring heat including a plurality of second containers, the second containers being freely flowable within the interior of the first container such that the second containers are readily movable relative to one another, said means for transferring heat further including a material conducive for heat transfer, at least some of the second containers being filled with said material, the first container being placeable on a living tissue region whereafter first and second containers conform to the tissue region, said means for transferring heat providing heat transfer between the first container and the tissue region to reduce at least one of pain and swelling in the tissue region; and
a tie device attached to edges of said first container device for supporting said first container, said tie device comprises extended portions of said first container device.

17. The heat transfer device of claim 16, wherein said tie device includes straps having a clip.

18. The heat transfer device of claim 16, wherein a majority of the second containers has a substantially spherical shape.

19. The heat transfer device of claim 16, wherein said material is water whereby said heat transfer device comprises at least one of being frozen and heated to initiate heat transfer between said first container and the tissue region.

20. A heat transfer device comprising:
a first container having an open interior, the first container being flexible; and
means for transferring heat including a plurality of second containers, the second containers being freely flowable within the interior of the first container such that the second containers are readily movable relative to one another, said means for transferring heat further including a material conducive for heat transfer, at least some of the second containers being filled with said material, the first container being placeable on a living tissue region whereafter first and second containers conform to the tissue region, said means for transferring heat providing heat transfer between the first container and the tissue region to reduce at least one of pain and swelling in the tissue region, said first container includes an outer fabric material on the surface of said first container, said fabric material comprises one of waterproof soft paper and moleskin.

21. The heat transfer device of claim 20, wherein a majority of the second containers has a substantially spherical shape.

22. The heat transfer device of claim 20, wherein said material is water whereby said heat transfer device comprises at least one of being frozen and heated to initiate heat transfer between said first container and the tissue region.

23. A method of reducing swelling with a heat transfer device, comprising the steps of:

placing a first container having a plurality of second spherical shaped containers disposed therein into at least one of a heating unit and a refrigerating unit;

placing said first container over a tissue region, conforming a shape of said first container and said second containers to said tissue region;

fastening said first container to said tissue region with a tie device, whereby said heat transfer device provides heat transfer between the first container and the tissue region to reduce at least one of pain and swelling in said tissue region, placing a third container having a plurality of said second spherical shaped containers disposed therein into at least one of a heating device and a refrigerating device;

placing said third container over a tissue region while attaching said third container to said first container by a hook and loop type fastener; and conforming a shape of said third container and said second containers to said tissue region.

* * * * *